Figure 1:
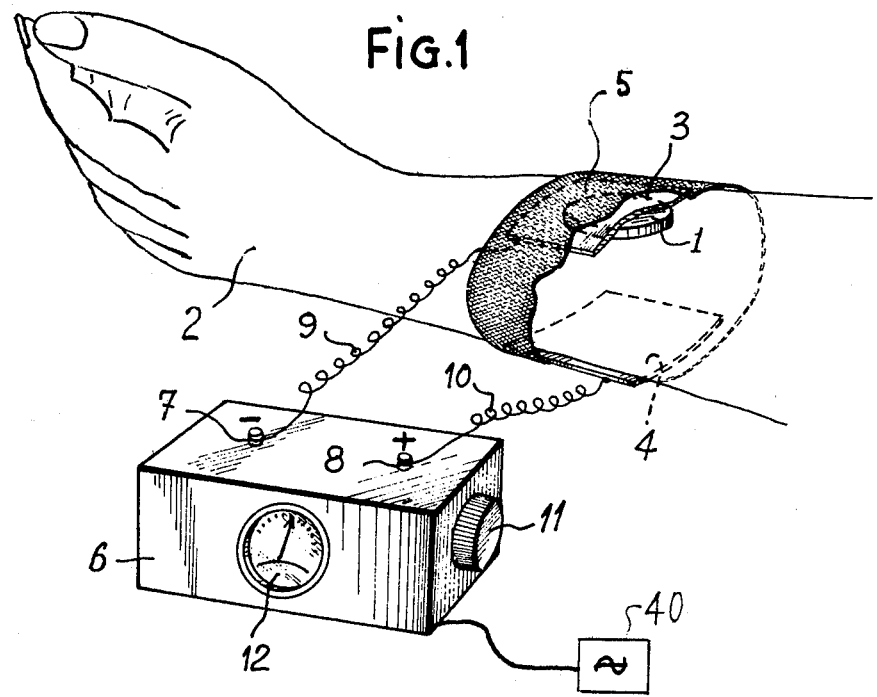

United States Patent [19]

Le Goaster

[11] 4,100,920

[45] Jul. 18, 1978

[54] METHOD AND APPARATUS FOR TRANSFERRING MICROORGANISMS THROUGH THE SKIN BARRIER

[76] Inventor: Jacqueline Marie George Juliette Le Goaster, 6, rue Raffet, 75016 Paris, Seine, France

[21] Appl. No.: 715,708

[22] Filed: Aug. 19, 1976

[30] Foreign Application Priority Data

Sep. 2, 1975 [FR] France .............................. 75 26888
Apr. 22, 1976 [FR] France .............................. 76 11924

[51] Int. Cl.$^2$ .............................................. A61N 1/30
[52] U.S. Cl. ................................ 128/172.1; 128/417; 128/419 R
[58] Field of Search ...................... 128/172.1, 362, 404, 128/405, 410, 411, 416, 417, 418, 419 R

[56] References Cited

U.S. PATENT DOCUMENTS

| 2,784,715 | 3/1957 | Kestler ............................. | 128/172.1 |
| 3,025,858 | 3/1962 | Browner ........................... | 128/418 X |
| 3,122,137 | 2/1964 | Erlanger ........................... | 128/172.1 |
| 3,289,671 | 12/1966 | Troutman et al. ............. | 128/172.1 X |
| 3,618,601 | 11/1971 | Richardson ..................... | 128/172.1 |
| 3,964,477 | 6/1976 | Ellis et al. ........................ | 128/172.1 |
| 3,991,755 | 11/1976 | Vernon et al. .................. | 128/172.1 |

OTHER PUBLICATIONS

*Essentials of Medical Electricity* by Cumberbatch, 1933, pp. 3–10, Henry Kimpton (publisher), London.
Spadaro et al., "Antibacterial Effects . . . Direct Current", Antimicrobial Agents and Chemotherapy, Nov. 1974, pp. 637–642, vol. 6, No. 5.

*Primary Examiner*—Robert W. Michell
*Assistant Examiner*—Lee S. Cohen
*Attorney, Agent, or Firm*—A. W. Breiner

[57] ABSTRACT

Method and system for transferring microorganisms through the skin barrier are described. The system comprises a pair of electrodes connected to a source of continuous current, a nutrient solution containing microorganisms and an impregnating spongy support located between at least one of the electrodes and the skin barrier. The microorganisms in the nutrient solution pass through the skin barrier under the action of an electrical field created by the electrodes. The method has application in the immunological treatment of tumorous diseases by means of Immuno-B.C.G.

18 Claims, 4 Drawing Figures

U.S. Patent  July 18, 1978  4,100,920

METHOD AND APPARATUS FOR TRANSFERRING MICROORGANISMS THROUGH THE SKIN BARRIER

The present invention relates to:
a method for transferring microorganisms through the skin barrier;
a therapeutical application of the said method for the immunological treatment of tumorous diseases;
an apparatus for the execution of the said method;
a compound (a complex product) conceived more particularly for the execution of the said method.

It has long been the desire of the physician to pass a variety of chemical compounds or products through the skin barrier without affecting the skin, mainly in order to expose human or animal cells to biological action for therapeutical purposes, or merely for purposes of embellishment, cleaning, etc.. However, it is also necessary to pass living microorganisms, such as bacteria, through the skin barrier, although not so frequently.

In certain cases it is desirable to administer living microorganisms transcutaneously. This is particularly so in the treatment of cancer by immunotherapy.

Thus for some ten years now, French and Anglo-Saxon researchers have been studying immunity-adjuvant therapy, i.e. therapy by stimulation of the person's natural defences which have been diminished by the tumorous disease from which he is suffering.

One of the immunity-adjuvants selected is B.C.G., Koch's bacillus, especially in the form more commonly known as Immuno-B.C.G..

The method at present in use for passing Immuno-B.C.G. (the living bacterium) through the skin barrier is the scarification method, which consists of scratching the skin in order to produce a bleeding serosity; there are two methods in general use:
the first consists in scratching the patient's skin manually with a needle over a square area, each side of which measures 5 cm, thus producing a scarification measuring about 1 meter in length;
the second method makes use of a mechanical scarifier (known in English as a "heaf-gun"), comprising a number of needles which perforate the skin.

Regardless of the method used, scarification has several disadvantages:
a. it is painful;
b. it is aesthetically unattractive, especially since the treatment requires a repetition every week in areas already scarified (the patient's limbs are literally tattooed);
c. the treatment requires the presence of a third party who must be willing, competent, and have served an apprenticeship.

There is thus a great need for a method which will allow microorganisms (such as those contained in Immuno-B.C.G.) to be transferred through the skin barrier without damaging it or changing its appearance.

There exists a prejudice against a concept of this nature. The skin barrier is known to be designed to prevent any bacterial invasion.

It would therefore appear, at first sight, inconceivable, if not impossible, to pass large numbers of living microorganisms through the skin barrier without first of all piercing it at least locally (as by scarification).

It is the purpose of the present invention to transfer microorganisms through the skin barrier without damaging the latter.

The basic characteristic of the invention is that it exposes the microorganisms located on one side of the skin barrier, namely the outside, to the action of an electrical field. According to one preferred form of execution, the method according to the invention comprises the following steps:
placing the microorganisms (such as Koch bacilli contained in Immuno-B.C.G.) in a nutrient medium containing active elements, and exposing them to the action of an electrical field;
applying the nutrient medium containing the microorganisms to the skin barrier;
exposing the microorganisms and their nutrient medium to the action of an electrical field.

The electrical field is preferably applied in a direction substantially perpendicular to the skin barrier.

Although it is known to make use of the effects of an electrical field upon an ionized, or ionizable, medium in order to cause the ions of which it consists to migrate through the skin barrier, methods of this kind being known to specialists as "dielectrolysis" or "ionophoresis", it should be noted that, prior to the invention, the use of an electrical field could be considered only in conjunction with solutions containing salts or ionizable compounds capable of being set in motion by the said electrical field. It was considered inconceivable, if not impossible, to apply this electrical procedure in conjunction with living organisms:
on the one hand, because it was not thought possible for a bacterium to respond to the action of an electrical field applied directly to it or to its environment, and
on the other hand, it was feared that the use of an electrical field would either kill the bacterium or modify its properties (for instance the immunological properties of the Koch bacillus contained in Immuno-B.C.G).

As indicated above, therefore, the physician was accustomed to passing microorganisms through the skin barrier by piercing the skin, and he was moreover prejudiced against procedures using an electrical field.

The method according to the present invention is therefore new, even revolutionary by certain standards, and it cannot be likened to any of the methods using dielectrolysis or ionophoresis known today.

The method of transferring microorganisms through the skin barrier according to the present invention may be used for a variety of purposes, namely for therapeutical purposes or for purposes of embellishment, for example to clean the patient's skin, or to eliminate the internal sources of certain visible blemishes. It has a very direct and important application in the immunological treatment of tumorous diseases. It has been stated above, for instance, that B.C.G. can be passed through the skin barrier by the method according to the invention. Now it is known that B.C.G., which is a live vaccine which has been in production since 1928 and the properties of which are known in connection with anti-tuberculosis vaccination, stimulates the white corpuscles, or macrophages, responsible for a person's immuno-defences. One of these B.C.G. vaccines, used in immuno-therapy and known more commonly under the name of "Immuno-B.C.G.", consists of particles of live Koch bacilli attenuated in an ionizable nutrient medium comprising glutamates.

The effective dose is about $6 \times 10^8$ living organisms per 1 $cm^3$ ampule. An ampule of Immuno-B.C.G. is applied by the method according to the invention, to a surface measuring about 5 × 5 cm² once weekly, to the upper and lower limbs alternately, in clockwise rotation, for a period of one year.

The present invention is also concerned with an apparatus for the execution of the method described above for transferring microorganisms through the skin barrier.

According to one essential characteristic, this apparatus comprises:
- on the one hand, a pair of electrodes connected to a source of continuous current (this part of the apparatus being designed to produce the electrical field in a manner known per se), and
- on the other hand, a nutrient solution containing the microorgansims.

The nutrient solution is applied to the skin barrier; one of the electrodes is applied to the part of the skin barrier to which the nutrient solution containing the microorganisms is applied; the other electrode is preferably applied to the skin barrier at a location opposite the first electrode.

A spongy supporting element, interposed between at least one of the electrodes and the skin barrier, is impregnated with the nutrient solution containing the microorganisms. In cases where the method according to the invention is to be used for the immunological treatment of tumorous diseases, and according to another essential characteristic of the invention, the apparatus for transferring Koch bacilli (especially in the form of Immuno-B.C.G.) through the skin barrier comprises:

on the one hand, one specific device comprising a pair of electrodes connected to a source of continuous current, and on the other hand, a plurality of unit doses of Koch bacilli, more particularly unit doses of Immuno-B.C.G., preferably in ampules of about 1 $cm^3$ capacity containing a nutrient solution in which the Koch bacilli are kept.

These unit doses are intended to be applied to the skin barrier at the moment when the method is to be put into use, more particularly by means of a sponge-like support impregnated with the content of the ampule. The electrodes are designed to be applied to the skin barrier; it should be noted, however, that in the case of Koch bacilli (Immuno-B.C.G.), the electrode connected to the negative terminal of the source of continuous current should be arranged upon that part of the skin barrier to which the immunizing dose of Immuno-B.C.G. is applied.

According to a secondary characteristic of the invention, the apparatus is also equipped with means for holding the electrodes to the skin barrier, the said means being preferably in the form of a strip of material adapted to be wound around the limb of the patient who is to receive the microorganisms; in this case, the said electrodes are secured to the internal surface of the strip of material, and the source of continuous current is preferably in the form of a battery attached to the said strip.

This arrangement provides a portable, self-contained unit which may easily be operated by the patient.

According to another secondary characteristic of the invention, the apparatus may be equipped with a means for adjusting the intensity of the current supplied by the source. Where the apparatus comprises a holding element in the form of a strip of material adapted to be wrapped around the patient's limb, the means of adjustment may be mounted directly upon the said strip of material.

The present invention is also concerned with a specific, portable, self-contained device designed especially to create the electrical field for the execution of the method.

This specific portable device comprises:

a holding element consisting of a strip of material designed to be wrapped around the patient's limb, and comprising a means for securing the said strip of material, preferably an adhesive system known under the trade mark of "VELCRO";

a pair of electrodes mounted upon one of the surfaces of the said strip of material and connected to a source of continuous current consisting of at least one battery also secured to the said strip of material.

Certain variants of this specific portable device may also be equipped with a means for controlling the intensity of the current supplied by the source of power. The electrodes of the device are preferably mounted upon the said strip of material, being arranged to face each other on opposite sides of the patient's limb, when the said strip is wrapped around the said limb.

The invention also relates to a compound specially designed for use in applying the method and comprising:

a nutrient medium containing living microorganisms;

elements responding to the action of an electrical field; these sensitive elements may be either the microorganisms themselves, if they possess this property, or ionizable elements associated with the said microorganisms, such as salts.

It will easily be appreciated that the methods and devices according to the invention, as described above, do not have the disadvantages of the scarifying processes set forth in *a.*, *b.*, *c.* above, it being obvious that the patient does not suffer, and that if he feels any slight discomfort (such as a burning or prickling sensation), he can always reduce the intensity of the current supplied by the source of power.

It is also obvious that, by its very nature, the method does not involve mechanical destruction of the skin barrier, and the patient is therefore not marked in any way.

Finally, the apparatus may easily be operated by the patient himself, without any previous training, especially if the said apparatus is equipped with the self-contained specific device described above. The patient may even travel with the apparatus and use it under any circumstances, wherever he may be.

A detailed description will now be given, by way of example and in conjunction with the drawing attached hereto:

on the one hand, of one example of embodiment and of the results which were observed and which prove that the method in question is effective, and on the other hand, of another example of embodiment, more particularly of a specific, self-contained device.

In the said drawing:

FIG. 1 is a broken-away perspective of a first example of embodiment, and application, of the apparatus and method according to the invention;

FIG. 2 is a perspective of another example of embodiment of the apparatus according to the invention;

FIG. **2*a*** illustrates a unit doses containing Immuno-B.C.G.;

Figure 2:
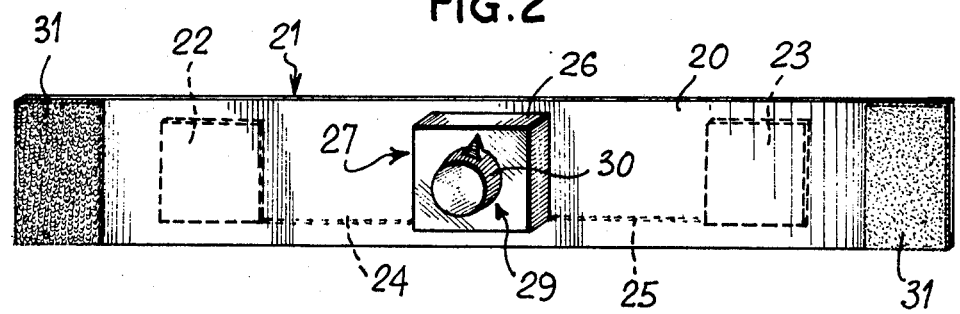
Figure 3:
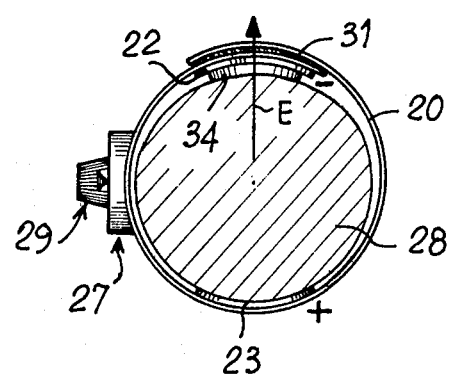

FIG. 3 is a cross-section of the specific, self-contained device according to FIG. 2, wrapped around the patient's arm.

A description will now be given of the apparatus illustrated in FIG. 1, and of the results observed after the method had been applied.

An inert cellulose pad 1, 2 cm in diameter and between 1 and 2 mm in thickness, is placed on the inside of the patient's forearm 2.

The content of an ampule of Immuno-B.C.G vaccine, having a capacity of about 1 cm³, is applied to the said inert cellulose pad, in such a manner that the said pad is impregnated therewith.

Two metal electrodes 3, 4 are arranged on each side of the forearm, one of them, 3, being in direct contact with the said cellulose pad and being connected to the negative terminal of a galvanic-current generator, while the other, 4, is held to the other side of the patient's forearm and is connected to the positive terminal of the said generator.

In order to facilitate the passage of the current, the electrodes are enclosed in spongy pouches carefully impregnated with water.

The electrodes are preferably made of aluminum or tin and are manipulated to fit the shape of the arm as far as possible.

The said electrodes may easily be kept in place by means of a strip of VELPEAU 5 applied not too tightly.

A suitable galvanic generator 6 is marketed under the trade mark "102 E.T.M. Galvanique", but any other direct-current generator may be used.

The negative 7 and positive 8 terminals of this generator are connected by leads 9, 10 respectively to electrodes 3, 4. The intensity of the electric current supplied by the generator will preferably be adjusted to between one and two milliamperes, in order to avoid discomfort to the patient. The operator must also be guided by the sensation of heat felt by the patient and he must adjust the power supplied by the generator by means of control element 11 fitted thereto. The intensity of the current being supplied is indicated by the ammeter 12.

The treatment lasts preferably for between 10 and 15 minutes, but this may vary, depending upon the individual patient and the intensity of the current.

Galvanic generator 102 E.T.M. is not self-contained, but must be connected, by means of a plug, to a 110/220V mains outlet 40. However, a self-contained, direct-current generator may obviously also be used, and an example of this will be described hereinafter in conjunction with FIG. 2.

Upon completion of the treatment, the following results are observed:
  a slight redness appears immediately opposite the area of skin treated;
  after 48 hours a deep-seated oedema forms and lasts for about 21 days.

This shows that the oedema is of bacterial origin — this reaction being of the immunizing type with delayed immunity. It is impossible to attribute this oedema to an immediate allergic hypersensitivity related to the nutrient medium containing the bacteria since, if this were so, the oedema would be resorbed within 1 to 9 days at the most.

As a result of this test it may therefore be stated that the bacteria contained in the Immuno-B.C.G. passes through the skin barrier and reaches, at a certain level, the superficial and intermediate dermis.

As a check, a second treatment may be carried out with the electrode polarity reversed, i.e. with the positive terminal connected to the pad impregnated with Immuno-B.C.G. This usually produces the following results: the red skin and oedema are observed, but the latter is obviously of the immediate hypersensitivity type, since it occurs immediately and disappears within 24 hours. It may therefore be concluded that, in this case, the bacteria failed to pass through the skin barrier. It would therefore appear that the sensitivity to an electrical field possessed by the bacteria contained in Immuno-B.C.G. varies according to the direction of the said field, i.e. according to the polarity thereof. It will be observed that the electrical field applied to Immuno-B.C.G. must be oriented towards the outside of the skin barrier.

A description will now be given of another example of embodiment of the apparatus according to the invention, in conjunction with FIGS. 2, 2a, and 3 which illustrate:
  on the one hand, a specific, self-contained device specially designed to create the electrical field required for the execution of the method according to the invention, and
  on the other hand, a plurality of unit doses of the compound to be transferred through the skin barrier.

The said specific, self-contained device has the advantage of allowing the patient himself to apply the immunological therapy for tumorous diseases, wherever he may be.

The said device consists of an armlet (or strip) 20, made of fabric or of a flexible plastic material, and of sufficient length to wrap around one of the patient's limbs (a thigh or an arm). One surface 21 of this armlet (not visible in FIG. 2) is equipped with two substantially rectangular metal electrodes 22, 23 measuring about 8 × 6 cm and spaced in relation to each other in such a manner that they are on each side of the patient's limb 28, when the armlet is wrapped around, as shown in FIG. 3. The electrodes, preferably made of aluminum or tin, are connected by two electric leads 24, 25, built into the said armlet, to a battery 26 located in a housing provided to this end in the said armlet.

The capacity of the battery is preferably sufficient to allow the apparatus to be used repeatedly for at least a year, at a rate of between 10 and 15 minutes weekly. It will be noted that in other examples of embodiment of the invention the battery is accomodated removably in a housing integral with the armlet, so that it may be replaced when it becomes exhausted. The battery used may be a dry battery or one adapted to be recharged by means of a device known per se plugged into the mains. According to another configuration of the apparatus, the dry battery or accumulator may be replaced by an auxiliary device which generates direct current, in a manner known per se, from the alternating current supplied by the mains, but in this case the apparatus and the method according to the invention can be used only where a mains outlet is available.

In the example of embodiment illustrated in FIGS. 2 and 3 of the self-contained device, an element 29 is provided for controlling the intensity of the current supplied by the battery. This element, known per se, may be in the form of a potentiometer bridge located between electrodes 22, 23 and the source 26 of direct current, the intensity of the current being controlled by means of a knurled knob 30. This element allows the operator to adjust the sensation of heat felt by the patient by varying the intensity of the current. However, in theory this control is not indispensable, since it is known in principle that the density of an electrical current that can be tolerated by a normal individual is of the order of 0.05 milliamperes/cm$^2$; the maximal current intensity may therefore be determined once and for all as a function of the area of the metal electrodes used. A source of direct current of about nine volts appears to be ample for most applications, as long as the person's ohmic resistance, with wet skin, does not exceed 600 ohms.

An arrangement 31 of the VELCRO type may be used to keep the strip of material wrapped around the patient's arm with the electrodes pressed to the skin. Obviously a system of hooks, with or without resilient means, may also be used for this purpose.

Moreover, in order to facilitate the passage of the electrical current, the metal electrodes (at least the electrode in direct contact with the skin) may be enclosed in a sponge pouch impregnated with tepid water.

Figure 2A:
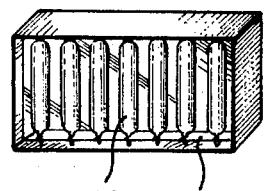

FIG. 2a shows a small box 32 containing a plurality of ampules 33, each having a capacity of about 1 cm$^3$ and containing a unit dose of Immuno-B.C.G.

A description will now be given of the manner in which the apparatus functions and is used.

The patient breaks an ampule 33 and uses the content to impregnate a sponge pad 34. He then places this pad on the inside surface of his forearm. He then applies the negative electrode (suitably marked with a minus sign) on the pad and wraps the strip of material relatively firmly around his forearm, making sure that the other electrode rests against the outside surface thereof. The electrical field produced by the device is directed as shown by arrow E in FIG. 3. The treatment period is of the order of 15 minutes, with a current intensity of about 1 to 2 milliamperes. It is to be understood that these figures may vary as a function of the electrical characteristics of the skin barriers of the persons to whom the treatment is applied.

In certain variants of the apparatus according to the invention, an electrical switch may be provided, although this is not indispensable. In order to facilitate the positioning of the pad impregnated with the Immuno-B.C.G., the internal surface of the electrode connected to the negative terminal may be provided with a cavity large enough to accomodate the said pad.

It should be noted that the element used to hold the electrodes to the patient's limb may be completely different from the one described herein; for instance, a pair of suction cups carrying the said electrodes may be used instead of the strip of material or the armlet.

The invention having now been disclosed, and its value justified by detailed examples, the Applicant hereby reserves exclusive rights thereto throughout the life of the patent, with no restrictions other than those imposed by the following claims.

What is claimed is

1. A method for transferring microorganisms through the skin barrier of a patient comprising the steps of exposing the microorganisms outside and in contact with the skin barrier to an electrical field of an intensity less than that which causes discomfort to the patient but sufficient to casue transfer of the microorganisms, and maintaining said exposure for a time sufficient for effective transfer of the microorganisms.

2. A method according to claim 1 further comprising before the step of exposing, the steps of placing the microorganisms in a nutrient medium containing elements responsive to the action of an electrical field, and applying the nutrient medium to the skin barrier.

3. A method according to claim 1 wherein the microorganisms are Immuno-B.C.G.

4. A method according to claim 1 wherein the electrical field is applied to a portion of skin barrier of about 5 × 5 cm and the intensity of the current is from about 1 to 2 mA.

5. A method according to claim 4 wherein the electrical field is applied for about 10 to about 15 minutes.

6. A method according to claim 1 wherein the electrical field is applied in a direction substantially perpendicular to the skin barrier.

7. A method according to claim 6 wherein the said electrical field is directed towards the outside of the skin barrier.

8. A method according to claim 7, for the immunological treatment of tumorous diseases, wherein the microorganisms used are immunity-adjuvant substances.

9. A system for transferring microorganisms through the skin barrier comprising a pair of electrodes, a source of continuous current, an electrical connection between said source and said electrodes, a nutrient solution containing the said microorganisms, the said nutrient solution being adapted to be applied to the skin barrier, and the said electrodes being adapted to be arranged against the skin barrier, at least one of the electrodes being adapted to be arranged upon the part of the skin barrier to which is applied the nutrient solution containing the said microorganisms during use, said at least one electrode containing said solution.

10. The system according to claim 9 wherein a spongy supporting element is impregnated with the said nutrient solution containing the said microorganisms, the said element contacting said at least one of the electrodes and being adapted to be interposed between said at least one electrode and the skin barrier during use.

11. The system according to claim 9 further comprising a retaining element supporting said electrodes and adapted to hold the electrodes firmly against the skin barrier.

12. The system according to claim 11 wherein said retaining element is in the form of a strip adapted to be wrapped around a patient's limb, the said electrodes being mounted upon the same face of the said strip, said face being adapted to be adjacent to the skin barrier during use, and the said source of current being in the form of a battery attached to the said strip, the system being portable and self-contained, and being easily operated by the patient.

13. The system according to claim 12 further comprising controlling means for controlling the intensity of the current supplied by the source of power.

14. The system according to claim 13 wherein the controlling means is mounted upon the said wraparound strip.

15. A system for transferring Immuno-B.C.G. through the skin barrier for the immunological treatment of tumorous diseases comprising a device comprising a pair of electrodes, a source of continuous current, and an electrical connection between said source and said electrodes, and at least a unit dose of Immuno-B.C.G. including a nutrient solution containing Koch bacilli, said unit dose being adapted to be applied to the skin barrier, and the said electrodes being adapted to be arranged against the skin barrier, the electrode connected to the negative terminal of the source of continuous current contacting the unit dose and being adapted to be arranged upon the part of the skin barrier to which a unit dose of Immuno-B.C.G is to be applied, during used.

16. The system according to claim 15 further comprising a spongy supporting element and wherein the said unit down impregnates said spongy supporting element, the said element contacting the electrode connected to the negative terminal and being adapted to be placed between the electrode connected to the negative terminal of the source of current and the skin barrier.

17. A method for transferring Koch bacilli, maintained in a supporting medium, through the skin barrier of a patient comprising the steps of applying the Koch bacilli, with the supporting medium, to the skin barrier, and exposing the Koch bacilli to the action of an electrical field of sufficient intensity to cause transfer of the Koch bacilli and for a time sufficient to effect transfer of the Koch bacilli.

18. A system for transferring an immunity-adjuvant, containing Koch bacilli, through the skin barrier, for the immunological treatment of tumorous diseases comprising a pair of electrodes, a source of continuous current, and an electrical connection between said source and said electrodes, at least a unit dose of the immunity-adjuvant consisting of a nutrient solution containing Koch bacilli, said unit dose being adapted to be applied to the skin barrier, and the electrode connected to the negative terminal of the source of continuous current contacting the Koch bacilli and being adapted to be arranged upon the part of the skin barrier to which said unit dose is to be applied during use.

* * * * *